(12) United States Patent
Morales-Ramos et al.

(10) Patent No.: US 8,025,027 B1
(45) Date of Patent: Sep. 27, 2011

(54) AUTOMATED INSECT SEPARATION SYSTEM

(75) Inventors: Juan A. Morales-Ramos, Greenville, MS (US); Maria G. Rojas, Greenville, MS (US); David I. Shapiro Ilan, Macon, GA (US); W. Louis Tedders, Perry, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 230 days.

(21) Appl. No.: 12/536,221

(22) Filed: Aug. 5, 2009

(51) Int. Cl.
*A01K 29/00* (2006.01)
(52) U.S. Cl. .......................................... 119/6.5; 119/6.7
(58) Field of Classification Search .................. 119/6.5, 119/6.6, 6.7; 209/311, 315–322, 325, 375
See application file for complete search history.

(56) References Cited

U.S. PATENT DOCUMENTS

| | | | | |
|---|---|---|---|---|
| 1,530,193 A | * | 3/1925 | Montgomery | 209/321 |
| 2,635,309 A | * | 4/1953 | Smith | 43/142 |
| 2,753,999 A | * | 7/1956 | Mathewson et al. | 209/403 |
| 3,794,165 A | * | 2/1974 | Riesbeck et al. | 209/325 |
| 3,960,329 A | * | 6/1976 | Aagaard | 241/19 |
| 4,076,124 A | * | 2/1978 | Taysom et al. | 209/665 |
| 7,591,375 B2 | * | 9/2009 | Johnson | 209/11 |
| 2003/0116477 A1 | * | 6/2003 | Brock et al. | 209/234 |
| 2003/0190860 A1 | * | 10/2003 | Vanderpool | 449/61 |
| 2008/0087581 A1 | * | 4/2008 | Eisenhut et al. | 209/318 |

* cited by examiner

*Primary Examiner* — T. Nguyen
(74) *Attorney, Agent, or Firm* — John D. Fado; Robert D. Jones

(57) ABSTRACT

The automated insect separation system processes an aggregate mixture of insects and other materials so that selected insects are separated from the other components of the mix. Specifically, the aggregate mix is directed into a separator apparatus so that the mix flows vertically through a series of vibrating screens. In the preferred embodiment, the screening process separates two different sizes of mealworm larvae from the aggregate mixture. The mix includes the mealworm larvae, unconsumed food materials (usually wheat bran), and insect frass.

9 Claims, 2 Drawing Sheets

AUTOMATED INSECT SEPARATION SYSTEM

FIELD OF THE INVENTION

The present invention relates to a system for separating insects from an aggregate mixture. Specifically, the invention relates to a step in the process of producing entomopathogenic nematodes wherein optimally-sized mealworm larvae are separated from an aggregate mixture comprising the larvae, unconsumed food materials and frass.

BACKGROUND OF THE INVENTION

For multiple reasons, farmers are seeking biologically-based pest control alternatives to commercial synthetic chemical pesticides. One "biocontrol" strategy is to increase the presence of the insects' natural enemies in the environment in which the crops are grown. These natural enemies may include beneficial entomopathogenic nematodes such as *Steinernema* spp or *Heterorhabditis* spp. These beneficial nematodes are parasites that prey on a variety of damaging insects but pose no danger to plants or humans.

Commercial production of beneficial nematodes can be in vitro (e.g., in fermentation tanks), or in vivo using susceptible insect hosts. Although both production systems have advantages, in vivo systems generally result in the production of better quality and more virulent nematodes. Further, more nematode species can be produced in vivo and in vivo production methods do not require the use of expensive and complex equipment.

However, in vivo production of beneficial nematodes requires the large scale production of an insect host that can be infected with the nematodes. Infection of a host insect allows the nematodes to multiply within the host's cadaver. After the hosts are infected and the nematodes begin to multiply, the infected cadavers are applied to the crop environment. Distributing the nematodes along with a food supply (i.e. the infected cadavers) increases the nematodes' survivability while the nematodes forage for damaging insects in their new crop environment.

Mealworm larvae (*Tenebrio molitor*) are ideal hosts for the nematodes. Mealworm larvae are relatively easy to mass produce, readily susceptible to infection by many nematode species, and the infected mealworm larvae cadavers are resilient enough to be manipulated without breakage or disintegration.

Mass production of the mealworm larvae involves mixing the larvae into a food aggregate where the larvae can grow and mature. However, the larvae develop at different rates so that there is always a range of larvae sizes in any mealworm aggregate mix. Removing the larvae from the food aggregate and separating out the optimal-sized larvae is a dirty and time-consuming process. In the past, workers have used progressively smaller manual sifters to hand-filter the aggregate mix and thereby separate out the larvae. However, in addition to being labor intensive, the sifting process results in dust and frass that becomes airborne. The resulting airborne particulate materials contaminate workers' immediate environment and potentially pose dangers to the workers' health.

The need exists for a quick, efficient, and automated system for separating optimally-sized mealworm larvae from an aggregate mix so that the nematode production process can proceed expeditiously. The current invention comprises a modular insect separator system and an associated process for moving relatively large volumes of aggregate mix through the system.

The preferred embodiment of the current system has the capacity to process up to 1,000,000 mealworm larvae per hour. The system separates the aggregate mix into: (1) mealworm larvae larger than 90 mg; (2) mealworm larvae between 70 mg and 90 mg; (3) unconsumed food materials and larvae smaller than 70 mg, and (4) insect frass.

While the preferred embodiment of the current invention is directed to the production of mealworm larvae for bio pest control purposes, the production and separation of other types of insects should be considered to be within the scope of the invention.

SUMMARY OF THE INVENTION

The current invention is directed to an insect separation system designed so that the system separates a selected insect out of an aggregate mix. The system includes a separator apparatus that has at least first and second screens arranged in series. Each of the screens has an associated separator aperture. Portions of the aggregate mix (which may include the selected insect) that are too large to pass through a respective screen are directed away from the screen and out of the separator.

The current invention is also directed to an insect separator apparatus. The separator apparatus includes a plurality of planar horizontally disposed screens with an inlet at the top of the separator apparatus. The screens are arranged in a vertical stack so that when an aggregate mix (which includes a selected insect) is deposited in the inlet, the screens selectively screen out the selected insect.

The current invention is further directed to a method of separating a selected insect from an aggregate mix that includes the insect. An automated separator apparatus with a plurality of planar, horizontally disposed screens is provided. The screens within the separator apparatus are arranged in a vertical stack. The aggregate mix is poured into an inlet at the top of the separator apparatus so that the mix is filtered by the screens. The screens are structured so that the selected insect is produced out of an aperture adjacent to a designated screen that is sized so that the selected insect cannot pass through the designated screen.

DETAILED DESCRIPTION OF PREFERRED EMBODIMENTS

The present invention is directed to an automated system that separates selected insects from an aggregate mix that includes the insects. Specifically, the system gently moves, cleans, and sorts two categories of commercial-sized mealworm larvae from the aggregate mixture. The mix includes the commercial-sized larvae, unconsumed food materials (usually wheat bran), smaller larvae, and insect frass.

Figure 1:
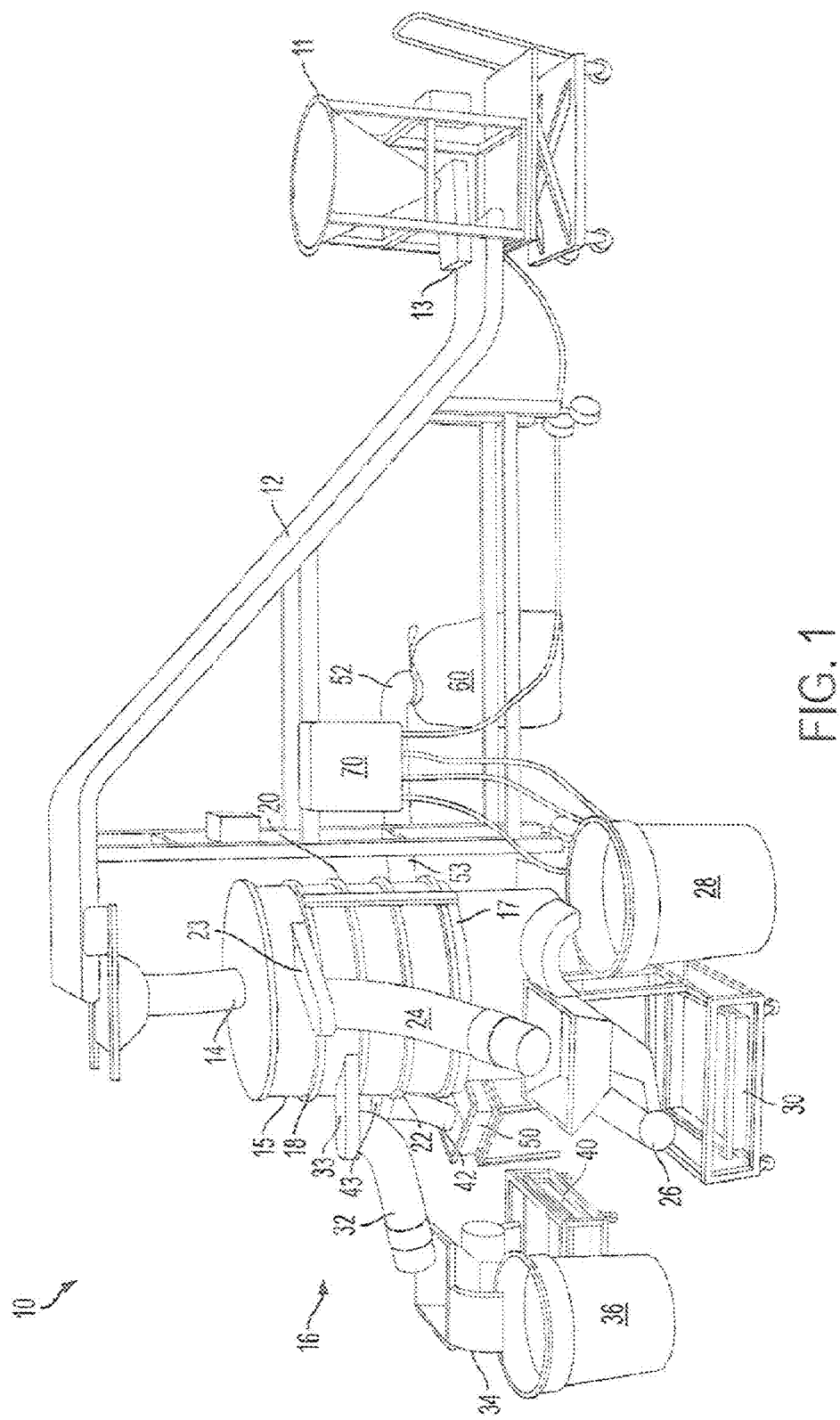
FIG. 1 is a perspective view of the automated insect separation system.
Figure 2:
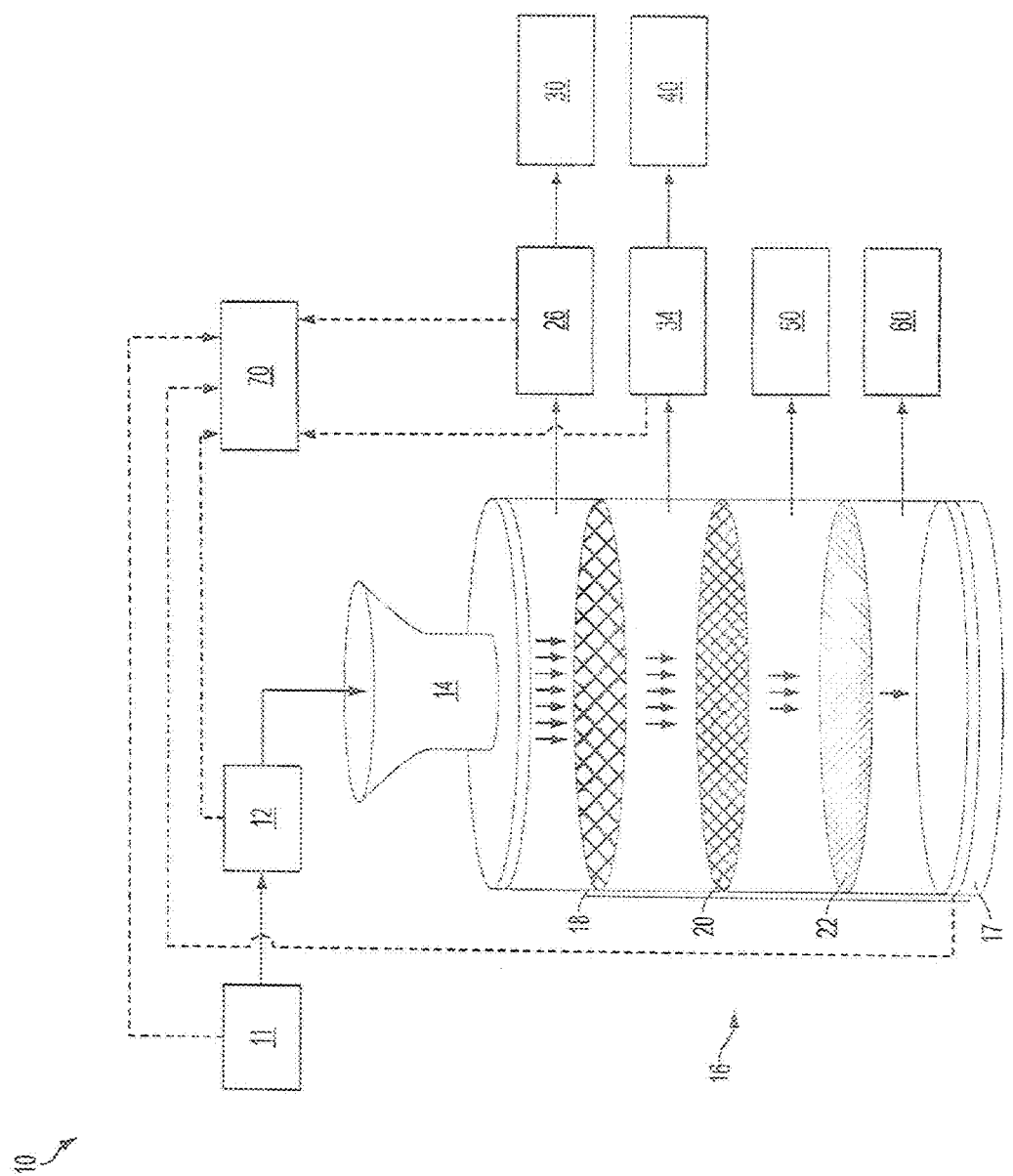
FIG. 2 is a schematic showing the principal components of the system as well as the flow of the aggregate mix through the system.

As generally shown in FIGS. 1 and 2, the current process is initiated by directing the aggregate mixture into the system 10. Specifically, mixture is poured into an electronically controllable hopper mechanism 11. The hopper mechanism 11 includes a hopper control and vibrating apparatus 13 that ensures that the hopper 11 does not become clogged and that the aggregate mixture flows out of the hopper 11 at a preselected rate.

The aggregate mixture is directed from the hopper 11 onto a z-shaped conveyor 12. The conveyor 12 transports the mixture upwardly to an inlet 14 of an enclosed modular separator apparatus 16. A housing 15 encloses the components of the separator apparatus 16. The separator apparatus 16 includes at least two screens that screen the incoming aggregate mix. A vibratory mechanism 17 imparts a radial vibration movement to each screen to ensure that the aggregate is thoroughly processed. As shown in FIGS. 1 and 2, in the preferred embodiment, the separator apparatus 16 comprises three screens 18, 20, 22. The dimensions of the first screen 18 are 0.073×0.500×30" so that the screen 18 has rectangular openings. The second screen 20 also has rectangular openings. The dimensions of the second screen are 0.065×0.500×30", and the third screen has square 500 µm (micron) openings.

In alternative embodiments, the number of screens and sizes and geometry of the screen openings can be varied so that the current invention produces modified results with the same or different insects. Further, for other applications, the induced vibrations may be amplified, modified, or deleted and multiple screens disposed adjacently or in close proximity may be used to create a more traditional sifting effect as opposed to the screening and filtering process of the preferred embodiment.

In the preferred embodiment, all the aggregate mix material passes through the first screen 18 with the exception of meal worm larvae larger than 90 mg. The induced vibrations eventually urge the 90 mg larvae out a first separator aperture 23 and down a first production chute 24. The first production chute 24 directs the larvae downwardly and through a traditional seed blower 26. The seed blower 26 cleans the larvae by blowing any particulate matter clinging to the larvae into a first waste receptacle 28. The cleaned mealworm larvae are then deposited in a first collection receptacle 30 for further processing.

Although these larvae may be used in the nematode rearing process, mealworm larvae larger than 90 mg are not the optimal size for the process. Larvae in this size range are more likely to be sold to pet stores, zoos, and animal sanctuaries as feeding materials for various birds, reptiles, tarantulas etc.

The aggregate mix passing through the first screen 18 is directed to the second screen 20. The second screen 20 is sized so that mealworm larvae from 70-90 mg are too large to pass through the second screen 20. The induced vibrations eventually urge the larvae that cannot pass through the second screen 20 out a second separator aperture 33 and down a second production chute 32. The second chute 32 directs the larvae downwardly and through a second seed blower 34. The seed blower 34 further cleans the larvae and blows any particulate matter into a second waste receptacle 36. The cleaned 70-90 mg mealworm larvae are then deposited in a second collection receptacle 40 for further processing. The 70-90 mg mealworm larvae are the optimal size for the mass rearing of beneficial nematodes.

The aggregate mix passing through the second screen 20 is similarly directed to the third screen 22. The third screen 22 is sized so that unconsumed food materials and mealworm larvae smaller than 70 mg are too large to pass through the third screen 22. The induced vibrations eventually urge the larvae that cannot pass through the third screen 22 towards a third separator aperture 43 and down a third production chute 42. The third chute 42 directs the larvae downwardly to a collection pan 50. The small mealworm larvae and the unconsumed food materials are simply deposited back into the mealworm larvae rearing area.

The frass passing through the third screen 22 is eventually directed through a fourth separator aperture 53 to a fourth production chute 52, which further directs the frass directly into a collection bag 60. In the preferred embodiment, the collection bag 60 is sealed to the fourth production chute 52 so that the frass is not allowed to contaminate the air around the separator apparatus 16. The collected frass may be used as an ingredient in organic fertilizers.

All the electro-mechanical components of the separator system can be controlled individually or collectively through a system controller 70. As shown in FIG. 1, in the preferred embodiment, the controller 70 is co-located with the system 10 and all system components are physically connected to the controller 70. In alternative embodiments, the controller 70 may be remotely located, or a remote operator may be in communication with the controller 70 through a wired or wireless network and the system 10 may be monitored through video cameras or sensors (or the like) that are accessible to the operator.

In further alternative embodiments, all aspects of the process are monitored and adjusted to optimize process efficiency and achieve a desired result. For example, the flow rate of the aggregate mix into the separator 16 may be monitored and modified as well as the flow rate of the respective products out of the separator 16. Additionally adjustable screening mechanisms may be used to automatically or manually adjust the size of the openings in the respective screens 18, 20, 22 so that the mix of resulting products may be varied. The induced vibration pattern and frequency, as well as the velocity of the seed blower air stream(s) may also modified to further optimize the process.

For the foregoing reasons, it is clear that the invention provides an innovative insect separation system that may be used in a variety of applications. The invention may be modified in multiple ways and applied in various technological applications. The current invention may be modified and customized as required by a specific operation or application, and the individual components may be modified and defined, as required, to achieve the desired result. Although the materials of construction are not described, they may include a variety of compositions consistent with the function of the invention. Such variations are not to be regarded as a departure from the spirit and scope of the invention, and all such modifications as would be obvious to one skilled in the art are intended to be included within the scope of the following claims.

What is claimed is:

1. An insect separation system comprising:
   an aggregate mix, wherein the aggregate mix comprises mealworm larvae, unconsumed mealworm larvae food, and frass;
   a separator apparatus, the separator apparatus comprising:
   (a) a first screen,
   (b) a first separator aperture, portions of the aggregate mix unable to pass through the first screen being directed away from the first screen through the first separator aperture,
   (c) a second screen in series with the first screen in which the first screen is disposed vertically above the second screen,
   (d) a second separator aperture, portions of the aggregate mix able to pass through the first screen but unable to pass through the second screen being directed away from the second screen and through the second separator aperture, (e) a third screen in series with the second screen in which the second screen is disposed vertically above the third screen,
(f) a third separator aperture, portions of the aggregate mix able to pass through the first and second screens but unable to pass through the third screen are directed away from the third screen and through the third separator aperture,
(g) a fourth separator aperture so that portions of the aggregate mix passing through the first, second, and third screens are directed to the fourth separator aperture,
wherein the aggregate mix is deposited into the separator apparatus and directed through the first screen then the second screen and then the third screen, the separator apparatus being structured so that mealworm larvae larger than 90 mg are produced from the first separator aperture, mealworm larvae from 70-90 mg are produced from the second separator aperture, mealworm larvae less than 70 mg and unconsumed mealworm larvae food are produced from the third separator aperture, and frass is produced from the fourth separator aperture;
a housing encloses the separator apparatus; and
a vibration inducing means so that vibrations are imparted to the first, second and third screens to facilitate the flow of the aggregate mix through the separator apparatus.

2. The system of claim 1 wherein rotary vibrations are imparted to the first and second screens.

3. The system of claim 1 wherein a vibrating and controllable hopper feeds the aggregate mix onto a z-shaped conveyor at pre-selected rates, the conveyor depositing the aggregate mix into the separator apparatus.

4. The system of claim 1 wherein the first separator aperture and the second separator aperture are connected to a first production chute and a second production chute respectively, a first air blower and a second air blower being in communication with the first production chute and the second production chute respectively, at least one of the first and second air blowers directing a stream of air over the selected insects to clean the selected insects of particulate matter, the selected insects being deposited in a collection receptacle.

5. The system of claim 4 wherein the first and second air blowers are seedblowers.

6. The system of claim 1 wherein the separator apparatus is controlled by a controller.

7. The system of claim 6 wherein the controller may be controlled by a remote means.

8. The system of claim 7 wherein the controller is one of programmable or capable of responding to computerized instructions so that the controller causes the separator to optimize production of the selected insects.

9. The system of claim 1 wherein the selected insects comprise 70-90 mg mealworm larvae.

\* \* \* \* \*